United States Patent [19]

Asato et al.

[11] 4,072,711

[45] Feb. 7, 1978

[54] TETRAHYDRO-4-SEMICARBAZONO-1-NAPHTHYLUREAS

[75] Inventors: Goro Asato, Titusville; Terence James Bentley, South Cranbury, both of N.J.

[73] Assignee: American Cyanamid Company, Stamford, Conn.

[21] Appl. No.: 781,232

[22] Filed: Mar. 25, 1977

Related U.S. Application Data

[62] Division of Ser. No. 705,313, July 14, 1976, Pat. No. 4,041,070.

[51] Int. Cl.$^2$ .................. C07C 133/08; C07C 157/09; A61K 31/175
[52] U.S. Cl. ............................ 260/554; 260/453 RW; 260/552 R; 260/453 A; 260/562 P; 260/578; 424/298; 424/323

[58] Field of Search ............... 260/554, 552 R, 553 A, 260/453 RW; 424/322, 323

[56] References Cited

U.S. PATENT DOCUMENTS

| | | | |
|---|---|---|---|
| 3,211,739 | 10/1965 | Schenker et al. | 260/558 R X |
| 3,769,341 | 10/1973 | Alt | 260/554 |
| 3,993,677 | 11/1976 | Asato | 260/553 A X |
| 4,005,140 | 1/1977 | Spicer et al. | 260/553 A |

*Primary Examiner*—Robert V. Hines
*Assistant Examiner*—Thomas A. Waltz
*Attorney, Agent, or Firm*—Harry H. Kline

[57] ABSTRACT

There are provided certain substituted-1,2,3,4-tetrahydro-4-imino-1-naphthylureas, methods of preparation thereof, and methods of use of said naphthylureas for enhancing feed efficiency and for promoting the growth rate of veterinary homothermic animals.

4 Claims, No Drawings

TETRAHYDRO-4-SEMICARBAZONO-1-NAPH-THYLUREAS

This application is a divisional of our co-pending application, Ser. No. 705,313, filed on July 14, 1976, now U.S. Pat. No. 4,041,070.

The present invention relates to novel substituted 1,2,3,4-tetrahydro-4-imino-1-naphthylureas and, more particularly, is concerned with compounds which may be represented by the following general formula:

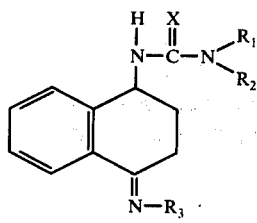

wherein X is oxygen or sulfur; $R_1$ is hydrogen or alkyl $C_1-C_4$; $R_2$ is hydrogen, alkyl $C_1-C_4$, 2-propynyl, alkoxy $C_1-C_4$ or benzyloxy; $R_3$ is a moiety represented by $-OR_4$,

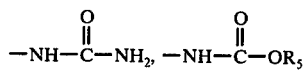

or $-N(CH_3)_2$; $R_4$ is hydrogen, alkyl $C_1-C_4$ or benzyl; $R_5$ is alkyl $C_1-C_4$, as well as the optical isomers along with racemic mixtures of the compounds of formula (I).

The optically active forms are designated as the (1R) and (1S) isomers, with the (1S) isomers being generally preferred, since they appear to be biologically more active than the (1R) forms. The (1S) isomers can be illustrated as follows:

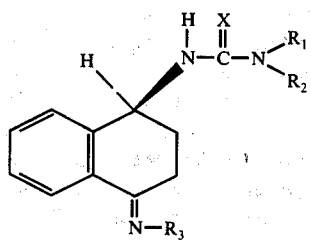

The (1R) isomers corresponding to the above (1S) isomers can be illustrated as follows:

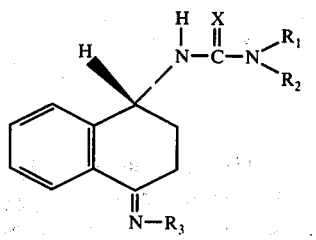

Hereinafter, the terms (R) and (S) will refer to the absolute configuration at the 1-position.

The above-identified optically active urea compounds represented by formulae (II) and (III) have the same absolute configuration at the 1-positions of the 1,2,3,4-tetrahydro-4-iminonaphthalene as the 1,2,3,4-tetrahydro-1-naphthylamine used as starting material. In order to obtain the formula (II) (S) isomer or the formula (III) (R) isomer, it is necessary to utilize the corresponding (S) or (R) isomer of 1,2,3,4-tetrahydro-1-naphthylamine or an appropriate derivative thereof.

Among the novel 1,2,3,4-tetrahydro-4-imino-1-naphthylurea compounds of formula (I), the most preferred group can be represented by formula (Ia) below:

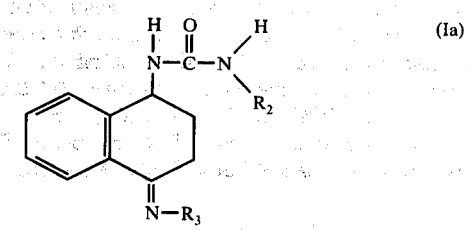

wherein $R_2$ is hydrogen or alkyl $C_1-C_4$; $R_3$ is a moiety represented by $-OR_4$,

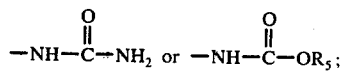

$R_4$ is hydrogen or alkyl $C_1-C_4$; $R_5$ is alkyl $C_1-C_4$; and said compounds are the racemic mixtures and the optical isomers thereof.

An especially preferred group of compounds of formula (I) can be represented by formula (Ib) below:

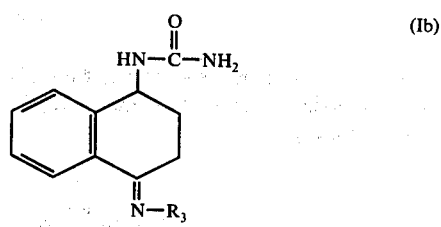

wherein $R_3$ is a moiety represented by $-OH$, $-OCH_3$,

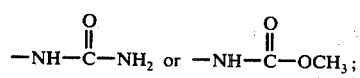

and said compounds are the racemic mixtures and the optical isomers thereof.

In accordance with the process of this invention, formula (I) 1,2,3,4-tetrahydro-4-imino-1-naphthylurea compounds wherein X, $R_1$, $R_2$ and $R_3$ are as hereinabove defined as well as the racemic mixtures and the optical isomers thereof, can be prepared in a straightforward manner from the corresponding 1,2,3,4-tetrahydro-4-oxo-1-naphthylurea compounds represented by formula (IV) below:

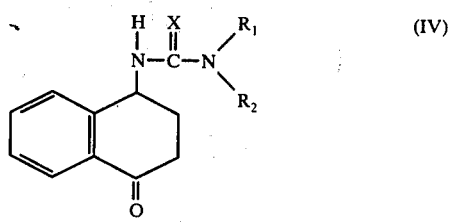

wherein X is oxygen or sulfur; $R_1$ is hydrogen or alkyl $C_1-C_4$; $R_2$ is hydrogen, alkyl $C_1-C_4$, 2-propynyl, alkoxy $C_1$–$C_4$ or benzyloxy; the racemic mixtures and the optical isomers thereof; by a plurality of procedures hereinbelow described and illustrated in detail.

Advantageously, a formula (I) tetrahydro-4-imino-1-naphthylurea compound wherein $R_3$ is —$OR_4$ and $R_1$, $R_2$ and $R_4$ are as defined above can be prepared by reacting 1 equivalent of a formula (IV) tetrahydro-4-oxo-1-naphthylurea with 1.0 to 1.2 equivalents of a compound of formula: $H_2N$—$OR_4$, or an acid addition salt (e.g. the hydrochloride) thereof in a $C_1$–$C_3$ aliphatic alcohol at a temperature from about 10° C to about 80° C and, preferably, from 50° C to 80° C, for from about 1 to 24 hours or until the reaction is essentially complete. The above reaction can be graphically illustrated as follows:

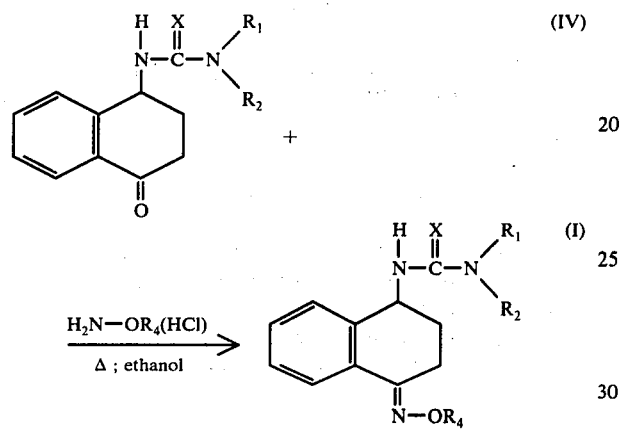

Utilizing analogous procedures, formula (I) 1,2,3,4-tetrahydro-4-imino-1-naphthylurea compounds can be obtained, wherein $R_3$ is

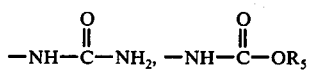

and —$N(CH_3)_2$; by the following generalized reaction scheme:

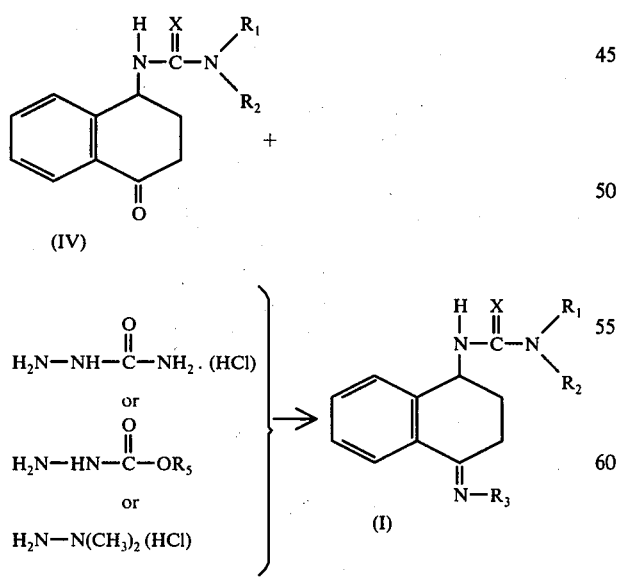

wherein X is oxygen or sulfur; $R_1$ is hydrogen or alkyl $C_1$–$C_4$; $R_2$ is hydrogen, alkyl $C_1$–$C_4$, 2-propynyl, alkoxy $C_1$–$C_4$ or benzyloxy; $R_5$ is alkyl $C_1$–$C_4$; $R_3$ is as hereinabove defined; and said compounds are the racemic mixtures and the optical isomers thereof.

The intermediate 1,2,3,4-tetrahydro-4-oxo-1-naphthylurea compound of formula (IV) can be conveniently prepared by reacting formula (V) 1,2,3,4-tetrahydro-4-oxo-1-naphthyl iso(thio)cyanate with an amine of formula:

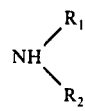

under standard laboratory conditions well-known in the art. This route can be graphically illustrated as follows:

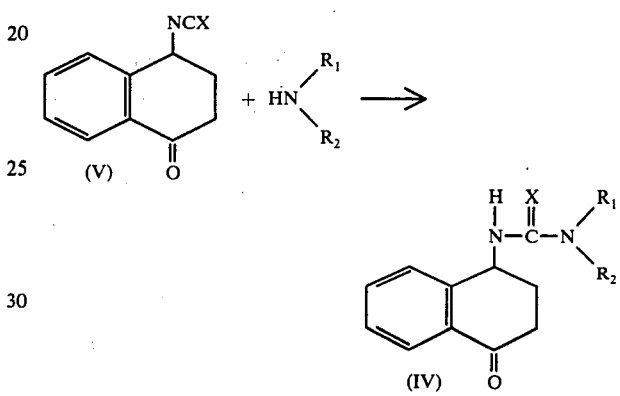

wherein X, $R_1$ and $R_2$ are hereinabove defined.

A formula (Va) isocyanate below can be prepared by reacting a formula (VI) amine or its acid addition salt with phosgene, preferably under anhydrous conditions, e.g. a blanket of inert gas, such as nitrogen. The reaction is initially carried out at a temperature between 0° C and 40° C, and preferably from 10° C to 20° C, and then heated to between about 50° C and 100° C, and preferably from 60° C to 80° C. The reaction is usually also conducted in the presence of an inert, organic solvent such as benzene, toluene or xylene. The reaction scheme is graphically illustrated below:

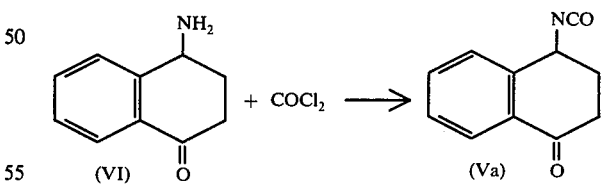

A formula (Vb) isothiocyanate can be prepared by reacting a formula (VI) amine with equimolar amounts of carbon disulfide, triethylamine and a caarbodiimide represented by the formula: G—N═C═N—G, where G is cyclohexyl, cycloheptyl, alkyl $C_4$–$C_6$ or the like. This reaction is usually conducted in the presence of a solvent such as tetrahydrofuran or an ether such as diethyl ether, at a temperature between —10° C and +25° C. The product can be isolated by distillation or by dry-column chromatography. The above reaction can be graphically illustrated as follows:

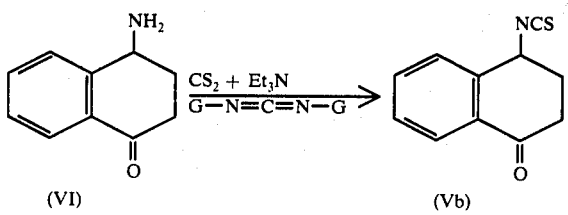

The precursor, formula (VI) 1,2,3,4-tetrahydro-4-oxo-1-naphthylamine, can be conveniently prepared by the route illustrated below:

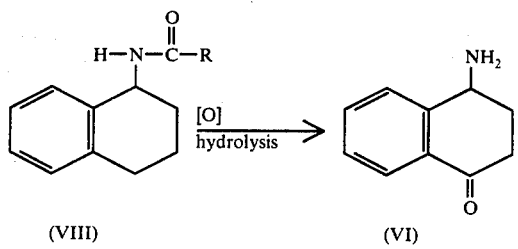

One equivalent of a formula (VII) compound, wherein R is hydrogen or alkyl $C_1$–$C_4$; is reacted with 2 to 8 equivalents and preferably with 3 to 5 equivalents of an oxidizing agent selected from the group consisting of ceric ammonium nitrate, ceric sulfate, chromic anhydride, sodium bichromate and the like, at a temperature between about 0° C and 100° C, and preferably 20° C to 60° C, in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or with the oxidizing agent chromic anhydride-acetic anhydride followed by hydrolysis.

Alternatively, the intermediate 1,2,3,4-tetrahydro-4-oxo-1-naphthylurea compound of formula (IV), where $R_1$ is hydrogen, can be prepared by reacting one equivalent of a formula (VI) amine with 1.0 to 1.5 equivalents of an iso(thio)cyanate of formula: $R_2NCX$. This route can be graphically illustrated as follows:

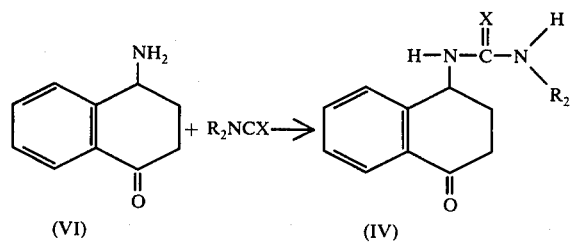

wherein X and $R_2$ are as hereinabove defined.

All of the hereinabove described reactions yield racemic compounds.

As stated above, to obtain the optically active forms of the novel formula (I) compounds, it is necessary to start with the corresponding optically active (S) or (R) isomer of 1,2,3,4-tetrahydro-1-naphthylamine or an appropriate derivative thereof.

A preparation is described hereinbelow whereby the desired optical isomers of the above-said amine or certain derivatives thereof can be obtained in high yields.

The racemic mixture is treated with the appropriate (optically active) N-benzoyl glutamic acid. The (S)-(+)-1,2,3,4-tetrahydro-1-naphthylamine forms a water insoluble salt with (+)-N-benzoyl-(R)-glutamic acid which can be crystallized out in high yield while the corresponding (R)-amine salt stays in solution. It is necessary to employ more than about one mole of the resolving acid for each two moles of racemic amine. A cheaper acid, preferably acetic, can be substituted for the balance of required acid. In this way, it is possible to obtain a high yield of the desired (S)-(+)-amine based on the resolving acid. The resolved salt, (S)-(+)-1,2,3,4-tetrahydro-1-naphthylamine (+)-N-benzoyl-(R)-glutamic acid salt, is treated with alkali which liberates the (S)-(+)-amine which separates as an insoluble phase. It can be mechanically separated from the aqueous phase or extracted with a suitable inert solvent, such as chloroform, methylene chloride or benzene.

As hereinabove stated, the novel compounds of the present invention represented by formula (I) below are useful as animal growth promoting agents.

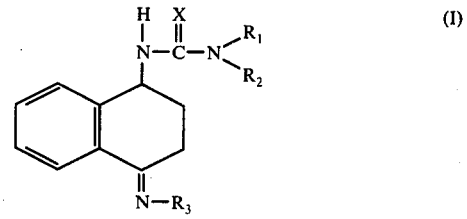

wherein X is oxygen or sulfur; $R_1$ is hydrogen or alkyl $C_1$–$C_4$; $R_2$ is hydrogen, alkyl $C_1$–$C_4$, 2-propynyl, alkoxy $C_1$–$C_4$ or benzyloxy; $R_3$ is a moiety such as $-OR_4$,

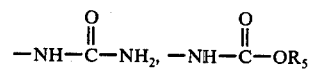

or $-N(CH_3)_2$; $R_4$ is hydrogen, alkyl $C_1$–$C_4$ or benzyl; $R_5$ is alkyl $C_1$–$C_4$; the racemic mixtures, and the optically active isomers thereof.

As animal growth-promoting agents, the active compounds of this invention can be administered to said animals in their diet, implanted in the form of one or several pellets under the skin of the animal, or injected subcutaneously or intramuscularly in the form of a paste, solution or suspension.

When administered with the animal diet, generally about 0.0001% to 0.08% by weight, and preferably 0.001% to 0.04% by weight, of the drug is effective for increasing weight gains of the treated animals. Advantageously, the compounds of the present invention can also be formulated as a premix, supplement or concentrate, with other edible carriers such as ground corn, soybean meal, fish meal and the like, and then mixed with or added to the animal feed at the feeding site. In such concentrated formulations, a compound of formula (I) 1,2,3,4-tetrahydro-4-imino-1-naphthylurea or its optically active isomer may amount from about 1% to 30% by weight of the formulation.

The growth rate of animals is also improved when a formula (I) 1,2,3,4-tetrahydro-4-imino-1-naphthylurea is administered as a subcutaneous implant under the skin of the animal. Implants are generally in the form of a paste or pellet which permits the active compound to be released into the bloodstream of the animal over an extended period of time; as for example, from several weeks to several months.

It is found that whether the implant is in the form of a paste or a pellet is a matter of choice. Pellet-type implants which can be used in accordance with this invention may be prepared by admixing from about 50% to 95% by weight of a compound of the formula (I) 1,2,3,4-tetrahydro-4-imino-1-naphthylurea compound or its optically active isomer with from about 50% to 5% by weight of a pharmaceutically acceptable carrier such as Castorwax (i.e., glyceryl 12-hydroxystearate), white wax, beeswax, starch, or a high molecular weight (i.e., 4000) polyethylene glycol, or mixtures thereof, alone or in combination with a small amount of a lubricant such as zinc stearate or magnesium stearate. A small amount of polyvinylpyrrolidone and dibutylphthalate may also be incorporated in the above-said formulations.

Paste implants can be prepared using the same percentages of drug as stated above, but employing a mixture of high molecular weight (i.e., 4000) polyethylene glycol and low molecular weight (i.e., 400) polyethylene glycol alone, or in combination with, Castorwax or beeswax and/or polyvinylpyrrolidone.

Implants may vary in size and weight, but usually range between 10 mg and 200 mg per implant. Advantageously, with this method of application, the drug can be administered at periodic intervals throughout the feeding period of the animals. Moreover, formulations and intervals between implantations can be varied to provide a daily drug release of generally about 0.0005 mg to 0.5 mg per kg of body weight, and preferably 0.001 mg to 0.2 mg per kg of body weight.

The present invention may be further understood by referring to the examples set forth below which are provided simply by way of illustration, and are not intended to limit the invention.

EXAMPLE 1

Preparation of N-(1,2,3,4-tetrahydro-4-oxo-1-naphthyl)formamide

A solution of 31.4 g of chromic anhydride in 140 ml of acetic anhydride is added dropwise over 80 minutes to a stirred solution of 20 g of N-(1,2,3,4-tetrahydro-1-naphthyl)-formamide in 120 ml of acetic anhydride, while maintaining the temperature of the reaction mixture between $-8°$ C and $4°$ C. The reaction mixture is then stirred an additional 35 minutes at $3°$ C, poured into an ice-water mixture and stirred overnight. The mixture is filtered and 1.5 g of solid collected. The filtrate is saturated with sodium chloride and extracted with $2 \times 1000$ ml of methylene chloride. The combined organic extracts are washed with 1000 ml of brine and evaporated to dryness in vacuo. The oily residue is triturated with 200 ml of ether to afford a tan solid, the mixture is stirred for a while and then filtered. The collected tan solid is washed with $2 \times 5$ ml of ether to afford 13 g of product, melting point $103°$ C to $106°$ C.

Substitution of sodium bichromate for chromic anhydride above also affords the desired compound.

The desired compound is also prepared by reacting N-(1,2,3,4-tetrahydro-1-naphthyl)formamide with four equivalents of ceric sulfate or ceric ammonium nitrate in 50% aqueous acid at room temperature for 10 minutes. The reaction mixture is then filtered, poured into water and extracted with chloroform. The chloroform extract is evaporated to dryness in vacuo to afford the title compound.

Similarly, (+)- and (−)-N-(1,2,3,4-tetrahydro-1-naphthyl)formamides are oxidized by the above procedures to afford (+)- and (−)-N-(1,2,3,4-tetrahydro-4-oxo-1-naphthyl)-formamides.

EXAMPLE 2

Preparation of 1,2,3,4-Tetrahydro-4-oxo-1-naphthylamine hydrochloride

A solution of 19.6 g of N-(1,2,3,4-tetrahydro-4-oxo-1-naphthyl)formamide in 214 ml of 95% ethanol and 214 ml of 2N hydrochloric acid is heated at reflux for 3 hours and then stirred at room temperature for 2 days. The solution is filtered and the filtrate concentrated in vacuo to afford a dark residue. The residue is dried using ethanol to remove water in vacuo and this procedure affords 20.2 g of the title compound, melting point $200°$ C to $216°$ C (dec.).

EXAMPLE 3

Preparation of 1,2,3,4-Tetrahydro-4-oxo-1-naphthylisocyanate

A mixture of 1,2,3,4-tetrahydro-4-oxo-1-naphthylamine hydrochloride (19.8 g) and 500 ml of toluene is stirred rapidly at $85°$ C and phosgene is bubbled into the mixture until a virtually clear solution forms. Nitrogen is passed through the solution, the mixture filtered to remove unreacted amine hydrochloride. The filtrate is evaporated to dryness in vacuo to afford 12.9 g of the desired isocyanate.

EXAMPLE 4

Preparation of 1,2,3,4-Tetrahydro-4-oxo-1-naphthylurea and thiourea intermediates The following intermediates (A) are prepared by reacting approximately equivalent amounts of 1,2,3,4-tetrahydro-4-oxo-1-naphthyl isocyanate (or thiocyanate) with the appropriate amines in methylene chloride according to the reaction scheme graphically illustrated below:

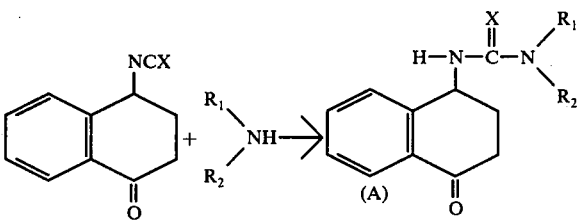

where $R_1$, $R_2$ and X are defined in the table below:

| $R_1$ | $R_2$ | X | Melting Point °C |
|---|---|---|---|
| H | CH$_3$ | O | 220–223 |
| 2-C$_4$H$_9$ | H | O | 176–178 |
| H | OCH$_3$ | O | 161–163 |
| H | OCH$_2$—⟨phenyl⟩ | O | 96–99 |
| H | C$_2$H$_5$ | S | 121–124 |
| H | CH$_2$—C≡CH | O | 173–177 |
| H | H | O | 241–244 (dec) |
| CH$_3$ | OCH$_3$ | O | 127–130 |
| CH$_3$ | CH$_3$ | O | 159–162 |
| CH$_3$ | CH$_3$ | S | Sticky Solid |

EXAMPLE 5

Preparation of Methyl-3-(3,4-dihydro-4-ureido-1(2H)-Naphthylidene)-carbazate A mixture of 1,2,3,4-tetrahydro-4-oxo-1-naphthylurea (4.5 g), methyl carbazate (4.0 g), 95% ethanol (150 ml) and concentrated hydrochloric acid (2 ml) is heated at reflux for an overnight period. The mixture is cooled to room temperature and the crystals are collected. The product melts at 230° C to 233° C (dec). On recrystallizing from aqueous methanol, the title compound melts at 223° C to 225° C (dec).

Similarly, substitution of methyl carbazate with n-butyl carbazate gives n-butyl-3-(3,4-dihydro-4-ureido-1(2H)-naphthylidene)carbazate.

By the above procedure, compounds of the following structure are prepared.

[Structure: naphthalene-based compound with H-N-C(=X)-N(R1)(R2) group and =N-N(H)-C(=O)-OR5 group]

| $R_1$ | $R_2$ | $R_5$ | X |
|---|---|---|---|
| H | $CH_3$ | $C_2H_5$ | O |
| H | $C_2H_5$ | $CH_3$ | O |
| $CH_3$ | $CH_3$ | $CH_3$ | O |
| n-$C_4H_9$ | H | $CH_3$ | O |
| H | H | n-$C_4H_9$ | O |
| H | $OCH_3$ | $CH_3$ | O |
| H | $OCH_2$-phenyl | $CH_3$ | O |
| H | $CH_2$-C≡CH | $CH_3$ | O |

EXAMPLE 6

Preparation of 1,2,3,4-Tetrahydro-4-oxo-1-naphthylurea, oxime

A mixture of 1,2,3,4-tetrahydro-4-oxo-1-naphthylurea (4.4 g), hydroxylamine hydrochloride (3.0 g) and 95% ethanol (150 ml) is heated at reflux for an hour on a steam bath. The mixture is evaporated to dryness in vacuo and the residue is stirred with water (50 ml). After an overnight period, the brown solid is collected; m.p. 193° C To 198° C (dec). The solid is recrystallized from ethanol to afford the title compound, m.p. 193° C to 198° C (dec). The analytically pure material melts at 209° C to 211° C (dec) after three recrystallizations.

By the above procedure, the following oximes are prepared:

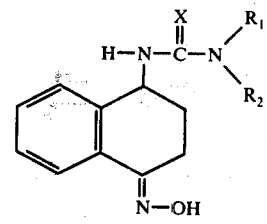

| $R_1$ | $R_2$ | X |
|---|---|---|
| $CH_3$ | $CH_3$ | O |
| H | $C_2H_5$ | S |
| n-$C_4H_9$ | H | O |
| H | i-$C_3H_7$ | O |
| H | n-$C_4H_9$ | S |
| H | $OCH_3$ | O |
| H | | O |
| H | $OCH_2$-phenyl | |
| H | $CH_2$-C≡CH | O |
| $CH_3$ | $OCH_3$ | O |

EXAMPLE 7

Preparation of 1,2,3,4-Tetrahydro-4-oxo-1-naphthylurea, thiosemicarbazone

A mixture of 1,2,3,4-tetrahydro-4-oxo-1-naphthylurea (5.8 g), thiosemicarbazide (5.2 g) and 95% ethanol (200 ml) are heated at reflux for 24 hours. The mixture is cooled and the crystals are collected to afford 7.1 g of title compound, m.p. 234° C (dec).

EXAMPLE 8

Preparation of 1,2,3,4-Tetrahydro-4-oxo-1-naphthylurea, O-methyloxime

A mixture of 1,2,3,4-tetrahydro-4-oxo-1-naphthylurea, methoxyamine hydrochloride (4.18 g) and 95% ethanol (150 ml) are heated at reflux for 1.5 hours on a steam bath. The mixture is then filtered and the filtrate evaporated to dryness in vacuo to afford a red, gummy residue. The gummy residue is stirred with water (~200 ml) and chloroform (~700 ml) added to the mixture. The emulsion formed is filtered, the chloroform phase separated and evaporated to yield 2.53 g of a solid (A), m.p. 190° C to 195° C. From the aqueous phase of the above filtrate 2.58 g of a solid (B) is isolated and found to be identical to solid (A). Recrystallization from acetone affords the title compound, m.p. 208° C to 209° C.

By the above procedure the following compounds are prepared, as shown below:

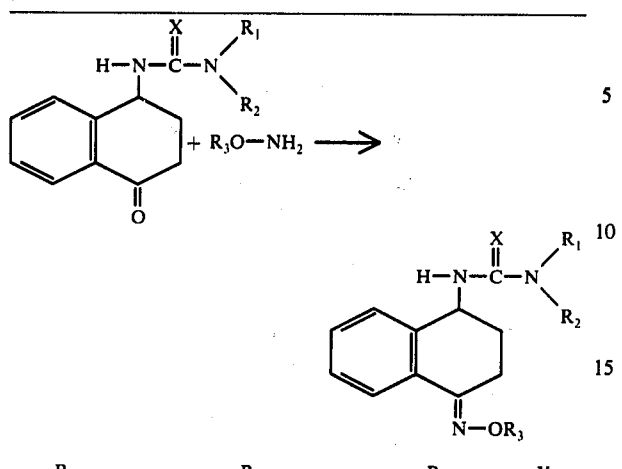

| $R_1$ | $R_2$ | $R_3$ | X |
|---|---|---|---|
| $CH_3$ | H | n-$C_4H_9$ | O |
| 2-$C_4H_9$ | H | $CH_3$ | O |
| i-$C_3H_7$ | H | $CH_3$ | O |
| $CH_3$ | $CH_3$ | $CH_3$ | O |
| $C_2H_5$ | H | $CH_3$ | S |
| H | $OCH_3$ | $C_2H_5$ | O |
| H | O—$CH_2$—C$_6$H$_5$ | $CH_3$ | O |
| $CH_3$ | $OCH_3$ | $CH_3$ | O |
| H | $CH_2$—C≡CH | $CH_3$ | O |
| H | H | n-$C_4H_9$ | O |

EXAMPLE 9

Preparation of 1,2,3,4-Tetrahydro-4-oxo-1-naphthylurea, semicarbazone

A mixture of 1,2,3,4-tetrahydro-4-oxo-1-naphthylurea (4.1 g), semicarbazide hydrochloride (3.34 g) and 95% ethanol (160 ml) is heated at reflux for 1.5 hours. The mixture is then cooled to room temperature and stirred overnight. The crystals are collected and dried to afford 4.8 g of title compound, m.p. 225° C to 233° C (dec). On recrystallizing from 50% aqueous acetic acid, the product melts at 232° C to 234° C (dec).

By the above procedure the following semicarbazones are prepared:

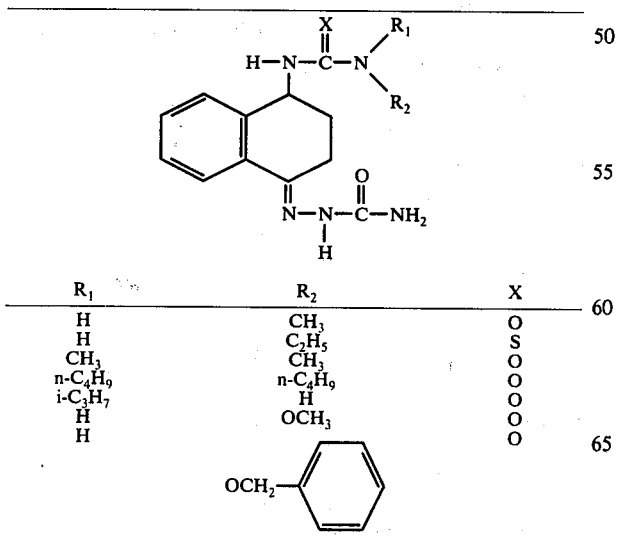

| $R_1$ | $R_2$ | X |
|---|---|---|
| H | $CH_3$ | O |
| H | $C_2H_5$ | S |
| $CH_3$ | $CH_3$ | O |
| n-$C_4H_9$ | n-$C_4H_9$ | O |
| i-$C_3H_7$ | H | O |
| H | $OCH_3$ | O |
| H | $OCH_2$—C$_6$H$_5$ | O |

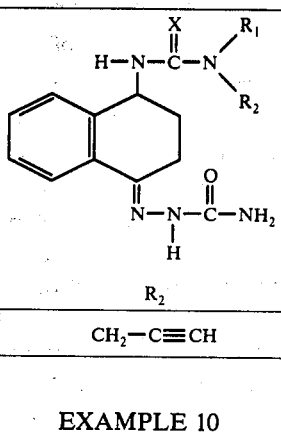

| $R_1$ | $R_2$ | X |
|---|---|---|
| H | $CH_2$—C≡CH | O |

EXAMPLE 10

Preparation of 1,2,3,4-Tetrahydro-4-oxo-1-naphthylurea, dimethylhydrazone

Equimolar amounts of 1,2,3,4-tetrahydro-4-oxo-1-naphthylurea and 1,1-dimethylhydrazine are stirred at room temperature in acetic acid for an overnight period. The mixture is evaporated to dryness in vacuo to afford a residue, which is stirred with water and then filtered to afford the title compound.

Similarly, the following hydrazones are prepared:

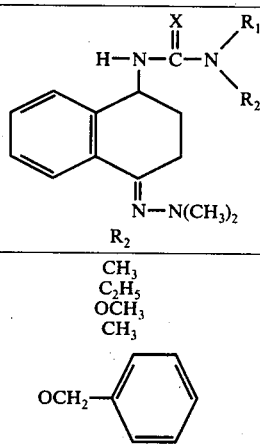

| $R_1$ | $R_2$ | X |
|---|---|---|
| H | $CH_3$ | O |
| H | $C_2H_5$ | S |
| H | $OCH_3$ | O |
| $CH_3$ | $CH_3$ | O |
| H | $OCH_2$—C$_6$H$_5$ | O |

EXAMPLE 11

Mouse Growth Regulant Tests

CFI female mice from Carworth Farm are received when they are 6 weeks old. They are housed 10 to a cage in air-conditioned rooms (72° F to 76° F) with automatically controlled lights, 14 hours on and 10 hours off. The basal diet used in these studies in Purina Laboratory Chow as defined hereinbelow which is supplied ad libitum. Water is also allowed ad libitum.

Thirteen days after arrival, the mice are weighed in groups of 10 and assigned at random to the different treatments. The concentration of the different compounds in the diet is indicated in the following Table. Twelve days later the mice are weighed again and the experiment terminated. At least 3 cages (30 mice) of untreated controls are included in each test. Test data are provided in Table I below, wherein data are reported as percent weight gain over controls. The following is a description of the diet to which the growth-promoting compounds are added.

DIET
GUARANTEED ANALYSIS

| | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, ioidized salt, ferric ammonium citrate, iron oxide, manganous oxide, cobalt carbonate, copper oxide, zinc oxide.

Table I

Effectiveness of 1,2,3,4-Tetrahydro-4-imino-1-naphthylureas as Animal Growth Promoting Agents Reported as Percent Weight Gain Over Controls Using Mice as the Test Animal

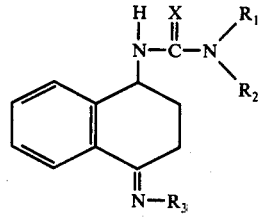

| Rate ppm In Diet | X | $R_1$ | $R_2$ | $R_3$ | % Weight Gain Over Controls |
|---|---|---|---|---|---|
| 400 | O | H | H | —OCH$_3$ | 14.9 |
| 400 | O | H | H | —NH—C(=O)—OCH$_3$ | 14.9 |
| 400 | O | H | H | —OH | 12.9 |
| 400 | O | H | H | —NH—C(=O)—NH$_2$ | 9.8 |

EXAMPLE 12

Preparation of 1-Isopropyl-3-(1,2,3,4-tetrahydro-4-oxo-1-naphthyl)urea

A 13 g sample of 1,2,3,4-tetrahydro-4-oxo-1-naphthylamine is dissolved in 100 ml of dichloromethane and stirred under nitrogen atmosphere. A solution of 6.86 g of isopropyl isocyanate in 45 ml of CH$_2$Cl$_2$ is then added over a 48 minute period at 20° C to 28° C. The mixture is stirred for 16 hours at room temperature and filtered to give the title compound, melting point 185° C to 188° C.

Similarly, substitution of isopropyl isocyanate with n-butyl isocyanate and n-butyl isothiocyanate affords 1-(n-butyl)-3-(1,2,3,4-tetrahydro-4-oxo-1-naphthyl)urea and 1-(n-butyl)-3-(1,2,3,4-tetrahydro-4-oxo-1-naphthyl)-thiourea, respectively.

EXAMPLE 13

Preparation of 1,1-Dimethyl-3-(1,2,3,4-tetrahydro-4-oxo-1-naphthyl)urea

In 25 ml of dichloromethane containing 2.8 ml of triethyl amine, 2,32 g of 1,2,3,4-tetrahydro-4-oxo-1-naphthylamine are added followed by 2.16 g of dimethylcarbamoyl chloride. The mixture is heated at reflux for 3 hours, cooled to room temperature, washed successively with 50 ml of H$_2$O, 50 ml of 3N NaOH, 50 ml of 3N HCl and 50 ml of H$_2$O. The organic phase is dried over magnesium sulfate and evaporated to dryness. The residue is recrystallized from toluene to give the title compound, melting point 157° C to 162° C.

Similarly, substitution of dimethylcarbamoyl chloride with diethyl- and di(n-butyl)carbamoyl chloride affords 1,1-diethyl- and 1,1-(n-dibutyl)-3-(1,2,3,4-tetrahydro-4-oxo-1-naphthyl)urea.

EXAMPLE 14

Preparation of 1,2,3,4-Tetrahydro-4-oxo-1-naphthyl isothiocyanate

A solution of 1,2,3,4-tetrahydro-4-oxo-1-naphthylamine (1.74 g) in ethyl acetate (25 ml) is stirred under a nitrogen atmosphere and triethylamine (1.37 ml) is added. The solution is cooled in ice-bath for 15 minutes and carbon disulfide (0.66 ml) added. A white precipitate forms. The mixture is stirred for 15 minutes at 5° C to 10° C and a solution of dicyclohexlcarbodiimide (2.1 g) in ethyl acetate (25 ml) is added dropwise. After stirring overnight, the reaction mixture is filtered and the filtrate evaporated to dryness in vacuo to afford the title isothiocyanate, which has an infrared absorption maximum at 2075 cm$^{-1}$.

We claim:

1. A compound of formula:

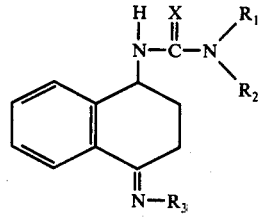

wherein X is oxygen or sulfur; $R_1$ is hydrogen or alkyl $C_1$–$C_4$; $R_2$ is hydrogen, alkyl $C_1$–$C_4$, 2-propynyl, alkoxy $C_1$–$C_4$ or benzyloxy; $R_3$ is the moiety

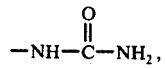

the racemic mixtures and the optical isomers thereof.

2. The compound according to claim 1, wherein X is oxygen; $R_1$ is hydrogen; $R_2$ is hydrogen or alkyl $C_1$–$C_4$; $R_3$ is the moiety

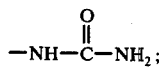

the racemic mixtures and the optical isomers thereof.

3. The compound according to claim 1, wherein X is oxygen; $R_1$ and $R_2$ are both hydrogen; $R_3$ is the moiety

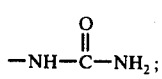

the racemic mixtures and the optical isomers thereof.

4. The compound according to claim 1, racemic 1,2,3,4-tetrahydro-4-oxo-1-naphthylurea-, semicarbazone; and the optical isomers thereof.

* * * * *